(12) United States Patent
Getto et al.

(10) Patent No.: US 9,466,151 B2
(45) Date of Patent: *Oct. 11, 2016

(54) BRACKET-SLOT-TO-WIRE PLAY COMPENSATION ARCHWIRE DESIGN

(75) Inventors: Phillip Getto, Plano, TX (US); Rohit Sachdeva, Plano, TX (US); Peer Sporbert, Berlin (DE); Dimitij Kouzian, Berlin (DE)

(73) Assignee: ORAMETRIX, INC., Richardson, TX (US)

( * ) Notice: Subject to any disclaimer, the term of this patent is extended or adjusted under 35 U.S.C. 154(b) by 370 days.

This patent is subject to a terminal disclaimer.

(21) Appl. No.: 12/772,133

(22) Filed: Apr. 30, 2010

(65) Prior Publication Data

US 2011/0267337 A1 Nov. 3, 2011

(51) Int. Cl.
| | |
|---|---|
| *G06F 17/50* | (2006.01) |
| *G06T 19/20* | (2011.01) |
| *A61C 7/00* | (2006.01) |
| *A61C 7/12* | (2006.01) |

(52) U.S. Cl.
CPC .............. *G06T 19/20* (2013.01); *A61C 7/002* (2013.01); *A61C 7/12* (2013.01); *G06T 2210/41* (2013.01)

(58) Field of Classification Search
CPC ........... G06F 17/5009; G06F 2217/16; G06F 19/20; G06F 2210/41; A61C 7/002; A61C 7/12
USPC ............................................................ 703/1
See application file for complete search history.

(56) References Cited

U.S. PATENT DOCUMENTS

| | | | |
|---|---|---|---|
| 6,632,089 B2 * | 10/2003 | Rubbert et al. ................. | 433/24 |
| 7,156,655 B2 * | 1/2007 | Sachdeva et al. .............. | 433/24 |
| 7,296,996 B2 * | 11/2007 | Sachdeva et al. .............. | 433/24 |
| 7,751,925 B2 * | 7/2010 | Rubbert et al. ............... | 700/162 |
| 8,192,197 B2 * | 6/2012 | Sporbert et al. ................ | 433/24 |
| 2003/0027098 A1 * | 2/2003 | Manemann et al. ........... | 433/24 |
| 2004/0029068 A1 * | 2/2004 | Sachdeva et al. .............. | 433/24 |
| 2004/0197727 A1 * | 10/2004 | Sachdeva et al. .............. | 433/24 |
| 2004/0214128 A1 * | 10/2004 | Sachdeva et al. .............. | 433/24 |
| 2009/0291417 A1 * | 11/2009 | Rubbert et al. ............... | 433/215 |
| 2011/0269097 A1 * | 11/2011 | Sporbert et al. ................ | 433/24 |

* cited by examiner

*Primary Examiner* — Dwin M Craig
(74) *Attorney, Agent, or Firm* — Jasvantrai C. Shah

(57) ABSTRACT

A method and workstation are described for designing compensation in an orthodontic archwire in order to offset the bracket-slot-to-wire play and realize the desired displacement in a tooth from an initial position to the target position. Bracket-slot-to-wire play can reduce the effectiveness of an archwire in bringing the teeth of an orthodontic patient from malocclusion to desired target. Bracket-slot-to-wire play is the difference in volume between the size of a bracket slot, which is larger than the size of the archwire, and the size of the sliding segment of an archwire inserted in the bracket slot. Customized archwires comprise alternating sliding segments interconnected by segments with bends and/or twists in three-dimensional space. The sliding segments are placed in the bracket slots and exert forces on the brackets created by the segments with bends and/or twists for moving the teeth towards the target positions.

41 Claims, 9 Drawing Sheets

BRACKET-SLOT-TO-WIRE PLAY COMPENSATION ARCHWIRE DESIGN

CROSS-REFERENCE TO RELATED APPLICATIONS

This application is related to application Ser. No. 10/428,461, filed May 2, 2003, pending, which is a continuation-in-part of application Ser. No. 09/834,412, filed Apr. 13, 2001, now issued as U.S. Pat. No. 6,632,089, the entire contents of which are incorporated by reference herein. This application is also related to patent application Ser. No. 10/429,123, filed May 2, 2003, now issued as U.S. Pat. No. 7,234,937, the entire contents of which are incorporated by reference herein. This application is also related to application Ser. No. 09/835,039, filed Apr. 13, 2001, now issued as U.S. Pat. No. 6,648,640, the entire contents of which are incorporated by reference herein.

BACKGROUND OF THE INVENTION

A. Field of the Invention

This invention relates generally to the field of orthodontics. More particularly, the invention relates to compensating the design of a customized archwire for treating an orthodontic patient in order to offset the bracket-slot-to-wire play resulting from smaller cross-sectional dimensions of the archwire compared to the dimensions of the bracket slot.

B. Description of Related Art

In orthodontics, a patient suffering from a malocclusion is typically treated by bonding brackets to the surface of the patient's teeth. The brackets have slots for receiving an archwire. The bracket-archwire interaction governs forces applied to the teeth and defines the desired direction of tooth movement. Typically, the bends in the wire are made manually by the orthodontist. During the course of treatment, the movement of the teeth is monitored. Corrections to the bracket position and/or wire shape are made manually by the orthodontist.

The key to efficiency in treatment and maximum quality in results is a realistic simulation of the treatment process. Today's orthodontists have the possibility of taking plaster models of the upper and lower jaw, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per jaw that covers all brackets and relevant portions of every tooth. Using such a transfer tray guarantees a very quick and yet precise bonding using indirect bonding.

However, it is obvious that such an approach requires an extreme amount of time and labor and thus is too costly, and this is the reason why it is not practiced widely. The normal orthodontist does not fabricate set-ups; he places the brackets directly on the patient's teeth to the best of his knowledge, uses an off-the-shelf wire and hopes for the best. There is no way to confirm whether the brackets are placed correctly; and misplacement of the bracket will change the direction and/or magnitude of the forces imparted on the teeth. While at the beginning of treatment things generally run well as all teeth start to move at least into the right direction, at the end of treatment a lot of time is lost by adaptations and corrections required due to the fact that the end result has not been properly planned at any point of time. For the orthodontist this is still preferable over the lab process described above, as the efforts for the lab process would still exceed the efforts that he has to put in during treatment. And the patient has no choice and does not know that treatment time could be significantly reduced if proper planning was done.

U.S. Pat. No. 5,431,562 to Andreiko et al. describes a computerized, appliance-driven approach to orthodontics. In this method, first certain shape information of teeth is acquired. A uniplanar target archform is calculated from the shape information. The shape of customized bracket slots, the bracket base, and the shape of an orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

More recently, in the late 1990's Align Technologies began offering transparent, removable aligning devices as a new treatment modality in orthodontics. In this system, a plaster model of the dentition of the patent is obtained by the orthodontist and shipped to a remote appliance manufacturing center, where it is scanned with a laser. A computer model of the dentition in a target situation is generated at the appliance manufacturing center and made available for viewing to the orthodontist over the Internet. The orthodontist indicates changes they wish to make to individual tooth positions. Later, another virtual model is provided over the Internet and the orthodontist reviews the revised model, and indicates any further changes. After several such iterations, the target situation is agreed upon. A series of removable aligning devices or shells are manufactured and delivered to the orthodontist. The shells, in theory, will move the patient's teeth to the desired or target position.

U.S. Pat. No. 6,632,089 to Rubbert discloses an interactive, software-based treatment planning method to correct a malocclusio. The method can be performed on an orthodontic workstation in a clinic or at a remote location such as a lab or precision appliance manufacturing center. The workstation stores a virtual three-dimensional model of the dentition of a patient and patient records. The virtual model is manipulated by the user to define a target situation for the patient, including a target archform and individual tooth positions in the archform. Parameters for an orthodontic appliance, such as the location of orthodontic brackets and resulting shape of a customized orthodontic archwire, are obtained from the simulation of tooth movement to the target situation and the placement position of virtual brackets.

However, the effectiveness of a customized archwire can be reduced when one or more archwire segments fail to engage the bracket slots properly due to the extra space surrounding the archwire segments occupying the bracket slots, since the archwires cross-sections are smaller in dimensions then the bracket slots they occupy. Therefore a need exists to for compensating the design of a customized archwire for treating an orthodontic patient in order to offset the bracket-slot-to-wire play resulting from smaller cross-sectional dimensions of the archwire compared to the dimensions of the bracket slot. The present invention meets this need.

SUMMARY OF THE INVENTION

The effectiveness of a customized archwire can be reduced when one or more archwire segments fail to engage the bracket slots properly due to the extra space surrounding the archwire segments occupying the bracket slots, since the archwires cross-sections are smaller in dimensions then the bracket slots they occupy. The space between a bracket slot and a sliding segment of the archwire occupying the bracket slot is hereinafter referred to as bracket-slot-to-wire play. The preferred embodiment of the invention disclosed herein teaches methods for offsetting the undesired effects of the bracket-slot-to-wire play by properly engaging the archwire in the bracket slots. The scope of the customized archwire design is expanded to include positioning the geometry of the archwire sliding segments in relation to the bracket slots in order to properly compensate for the bracket-slot-to-wire play.

As a typical deficiency, the bracket-slot-to-wire play prevents an archwire from exerting the desired torque to move a tooth in the facial or lingual direction. According to the preferred embodiment of the invention, this deficiency can be offset by applying proper amount of rotation or twist to the sliding segment of the archwire along the long axis of the wire or x-axis.

As another deficiency, the bracket-slot-to-wire play prevents an archwire from exerting the desired angulation force to move a tooth in the mesial or distal direction. According to another preferred embodiment of the invention, this deficiency can be offset by applying proper amount of rotation or twist to the sliding segment of the archwire around the y-axis of the wire.

As yet another deficiency, the bracket-slot-to-wire play prevents an archwire from exerting the desired force to rotate a tooth in the mesial or distal direction. According to yet another preferred embodiment of the invention, this deficiency can be offset by applying proper amount of rotation or twist to the sliding segment of the archwire around z-axis.

As yet another deficiency, the bracket-slot-to-wire play prevents an archwire from exerting the desired translational force to move a tooth in the buccal or lingual direction. According to yet another preferred embodiment of the invention, this deficiency can be offset by applying proper amount of translation movement to the sliding segment of the archwire along y-axis.

As yet another deficiency, the bracket-slot-to-wire play prevents an archwire from exerting the desired translational force to move a tooth in the occlusal or gingival direction. According to yet another preferred embodiment of the invention, this deficiency can be offset by applying proper amount of translation movement to the sliding segment of the archwire along z-axis.

In summary, the deficiencies caused by the bracket-slot-to-wire play by disabling an archwire from exerting the desired force in any of the 5-degrees of freedom, namely torque (facial and lingual), angulation (mesial and distal), rotation (mesial and distal), buccal and lingual translation and occlusal and gingival translation, can be offset by the various embodiments of the invention disclosed above. A user can manually or automatically identify the type of deficiency caused by the bracket-slot-to-wire play, given bracket slot size and the archwire cross section parameters, and manually or automatically determine the method of offsetting the deficiency, by using the software tools available in the treatment planning workstation. The desired offset for the compensation of the bracket-slot-to-wire play is displayed on the display of the treatment planning workstation. The user can override the offset automatically determined by the treatment planning software and simulate and design the archwire based upon the offset determined to be more desirable by the treatment planner or the practitioner. If the desired tooth position cannot be achieved with a single offset, then the practitioner may choose to accomplish that in multiple stages of the tooth movement during the course of the treatment by changing the design of the archwire as the treatment progresses. Also, it is possible that multiple types of deficiencies may be caused by the bracket-slot-to-wire play. In that case the practitioner may choose to combine the remedies for one or more deficiencies using the procedure described above for each degree of freedom, i.e. torque, angulation, rotation and buccal-lingual and occlusal-gingival translations; or approach the remedies in treatment stages.

In summary then, according to the preferred embodiment of the invention, the procedure described below is utilized to realize compensation for the bracket-slot-to-wire play.

1. Quantify the bracket-slot-to-wire play.
   (a) This can be accomplished if one of the following items is known.
      i. ideal slot size and ideal archwire cross-section;
      ii. tolerance model of slot and tolerance model of the archwire cross-section;
      iii. actual (measured) model of slot and actual (measured) model of the archwire cross-section (for each individual item or on a lot bases); or
      iv. every possible combination of the above three items.
   (b) It can be determined from the actual and target positions of bracket slots.
2. Then the offset to compensate for the bracket-slot-to-wire play can be determined as follows:
   a. Calculate the slot play between the bracket-slot and the height of the archwire.
   b. Calculate the direction of the intended movement in coordinates of the bracket slot. (i.e., initial or actual to target or set-up)
   c. Calculate the maximum possible rotation or translation of the archwire sliding segment in the bracket-slot, so that the sides or the edges of the archwire touch the sides of the walls of the bracket-slot, based upon the direction of the information from step 2.b.

BRIEF DESCRIPTION OF THE DRAWINGS

Presently preferred embodiments of the invention are described below in reference to the appended drawings, wherein like reference numerals refer to like elements in the various views, and in which:

FIG. 5 also shows the slot for the bracket associated with the tooth and the archwire cross-section rotated to deliver the desired facial torque.

FIG. 6 shows the same example tooth as in FIG. 5. However, the practitioner overrides the automatic determination by the treatment planning software and changes the torque to a lingual torque. FIG. 6 shows the same slot for the bracket as in FIG. 5 associated with the tooth. However, the archwire cross-section is now rotated in the lingual direction to deliver the desired lingual torque.

FIG. 7 shows the same example tooth as in FIG. 5. The tooth is shown in two different positions, namely the tooth in the target position superimposed over the tooth in the initial position, in FIG. 7. Also shown are the bracket and the archwire cross-section rotated to deliver facial torque.

DETAILED DESCRIPTION OF PREFERRED EMBODIMENT

Before describing the features of this invention in detail, an overview of a unified workstation will be set forth initially. The workstation provides software features that create two dimensional and/or three-dimensional virtual patient model on a computer, which can be used for purposes of treatment planning in accordance with a presently preferred embodiment.

Many of the details and computer user interface tools which a practitioner may use in adjusting tooth position, designing appliance shape and location, managing space between teeth, and arriving at a finish tooth position using interaction with a computer storing and displaying a virtual model of teeth are set forth in the prior application Ser. No. 09/834,412 filed Apr. 13, 2001, and in published OraMetrix patent application WO 01/80761, the contents of which are incorporated by reference herein. Other suites of tools and functions are possible and within the scope of the invention. Such details will therefore be omitted from the present discussion.

General Description

A unified workstation environment and computer system for diagnosis, treatment planning and delivery of therapeutics, especially adapted for treatment of craniofacial structures, is described below. In one possible example, the system is particularly useful in diagnosis and planning treatment of an orthodontic patient. Persons skilled in the art will understand that the invention, in its broader aspects, is applicable to other craniofacial disorders or conditions requiring surgery, prosthodontic treatment, restorative treatment, etc.

Figure 1:
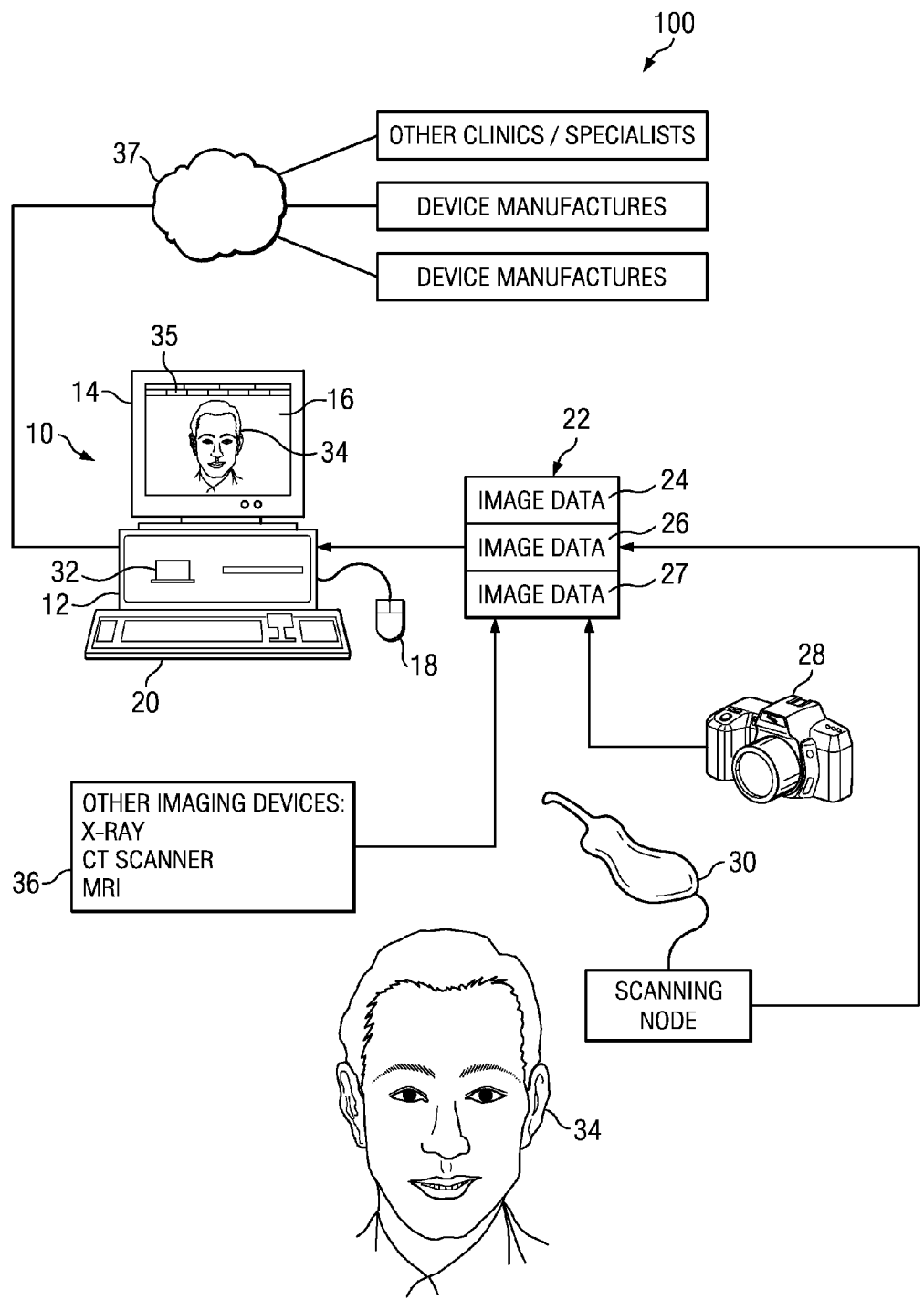
FIG. 1 is block diagram of a system for creating a three-dimensional virtual patient model and for diagnosis and planning treatment of the patient.

A presently preferred embodiment is depicted in FIG. 1. The overall system 100 includes a general-purpose computer system 10 having a processor (CPU 12) and a user interface 14, including screen display 16, mouse 18 and keyboard 20. The system is useful for planning treatment for a patient 34.

The system 100 includes a computer storage medium or memory 22 accessible to the general-purpose computer system 10. The memory 22, such as a hard disk memory or attached peripheral devices, stores two or more sets of digital data representing patient craniofacial image information. These sets include at least a first set of digital data 24 representing patient craniofacial image information obtained from a first imaging device and a second set of digital data 26 representing patient craniofacial image information obtained from a second image device different from the first image device. The first and second sets of data represent, at least in part, common craniofacial anatomical structures of the patient. At least one of the first and second sets of digital data normally would include data representing the external visual appearance or surface configuration of the face of the patient.

In a representative and non-limiting example of the data sets, the first data set 24 could be a set of two dimensional color photographs of the face and head of the patient obtained via a color digital camera 28, and the second data set is three-dimensional image information of the patient's teeth, acquired via a suitable scanner 30, such as a hand-held optical 3D scanner, or other type of scanner. The memory 22 may also store other sets 27 of digital image data, including digitized X-rays, MRI or ultrasound images, CT scanner etc., from other imaging devices 36. The other imaging devices need not be located at the location or site of the workstation system 100. Rather, the imaging of the patient 34 with one or other imaging devices 36 could be performed in a remotely located clinic or hospital, in which case the image data is obtained by the workstation 100 over the Internet 37 or some other communications medium, and stored in the memory 22.

The system 100 further includes a set of computer instructions stored on a machine-readable storage medium. The instructions may be stored in the memory 22 accessible to the general-purpose computer system 10. The machine-readable medium storing the instructions may alternatively be a hard disk memory 32 for the computer system 10, external memory devices, or may be resident on a file server on a network connected to the computer system, the details of which are not important. The set of instructions, described in more detail below, comprise instructions for causing the general computer system 10 to perform several functions related to the generation and use of the virtual patient model in diagnostics, therapeutics and treatment planning.

These functions include a function of automatically, and/or with the aid of operator interaction via the user interface 14, superimposing the first set 24 of digital data and the second set 26 of digital data so as to provide a composite, combined digital representation of the craniofacial anatomical structures in a common coordinate system. This composite, combined digital representation is referred to herein occasionally as the "virtual patient model," shown on the display 16 of FIG. 1 as a digital model of the patient 34. Preferably, one of the sets 24, 26 of data includes photographic image data of the patient's face, teeth and head, obtained with the color digital camera 28. The other set of data could be intra-oral 3D scan data obtained from the hand-held scanner 30, CT scan data, X-Ray data, MRI, etc. In the example of FIG. 1, the hand-held scanner 30 acquires a series of images containing 3D information and this information is used to generate a 3D model in the scanning node 31, in accordance with the teachings of the published PCT application of OraMetrix, PCT publication no. WO 01/80761, the content of which is incorporated by reference herein. Additional data sets are possible, and may be preferred in most embodiments. For example the virtual patient model could be created by a superposition of the following data sets: intra-oral scan of the patient's teeth, gums, and associated tissues, X-Ray, CT scan, intra-oral color photographs of the teeth to add true color (texture) to the 3D teeth models, and color photographs of the face, that are combined in the computer to form a 3D morphable face model. These data sets are superimposed with each other, with appropriate scaling as necessary to place them in registry with each other and at the same scale. The resulting representation can be stored as a 3D point cloud representing not only the surface on the patient but also interior structures, such as tooth roots, bone, and other structures. In one possible embodiment, the hand-held in-vivo scanning device is used which also incorporates a color CCD camera to capture either individual images or video.

The software instructions further includes a set of functions or routines that cause the user interface 16 to display the composite, combined digital three-dimensional representation of craniofacial anatomical structures to a user of the system. In a representative embodiment, computer-aided design (CAD)-type software tools are used to display the model to the user and provide the user with tools for viewing and studying the model. Preferably, the model is cable of being viewed in any orientation. Tools are provided for showing slices or sections through the model at arbitrary, user defined planes. Alternatively, the composite digital representation may be printed out on a printer or otherwise provided to the user in a visual form.

The software instructions further include instructions that, when executed, provide the user with tools on the user interface 14 for visually studying, on the user interface, the interaction of the craniofacial anatomical structures and their relationship to the external, visual appearance of the patient. For example, the tools include tools for simulating changes in the anatomical position or shape of the craniofacial anatomical structures, e.g., teeth, jaw, bone or soft tissue structure, and their effect on the external, visual appearance of the patient. The preferred aspects of the software tools include tools for manipulating various parameters such as the age of the patient; the position, orientation, color and texture of the teeth; reflectivity and ambient conditions of light and its effect on visual appearance. The elements of the craniofacial and dental complex can be analyzed quickly in either static format (i.e., no movement of the anatomical structures relative to each other) or in an dynamic format (i.e., during movement of anatomical structures relative to each other, such as chewing, occlusion, growth, etc.). To facilitate such modeling and simulations, teeth may be modeled as independent, individually moveable 3 dimensional virtual objects, using the techniques described in the above-referenced OraMetrix published PCT application, WO 01/80761.

The workstation environment provided by this invention provides a powerful system and for purposes of diagnosis, treatment planning and delivery of therapeutics. For example, the effect of jaw and skull movement on the patient's face and smile can be studied. Similarly, the model can be manipulated to arrive at the patient's desired feature and smile. From this model, and more particularly, from the location and position of individual anatomical structures (e.g., individual tooth positions and orientation, shape of arch and position of upper and lower arches relative to each other), it is possible to automatically back solve for or derive the jaw, tooth, bone and/or soft tissue corrections that must be applied to the patient's initial, pre-treatment position to provide the desired result. This leads directly to a patient treatment plan.

These simulation tools, in a preferred embodiment, comprise user-friendly and intuitive icons 35 that are activated by a mouse or keyboard on the user interface of the computer system 10. When these icons are activated, the software instruction provide pop-up, menu, or other types screens that enable a user to navigate through particular tasks to highlight and select individual anatomical features, change their positions relative to other structures, and simulate movement of the jaws (chewing or occlusion). Examples of the types of navigational tools, icons and treatment planning tools for a computer user interface that may be useful in this process and provide a point of departure for further types of displays useful in this invention are described in the patent application of Rudger Rubbert et al., Ser. No. 09/835,039 filed Apr. 13, 2001, the contents of which are incorporated by reference herein.

The virtual patient model, or some portion thereof, such as data describing a three-dimensional model of the teeth in initial and target or treatment positions, is useful information for generating customized orthodontic appliances for treatment of the patient. The position of the teeth in the initial and desired positions can be used to generate a set of customized brackets, and customized flat planar archwire, and customized bracket placement jigs, as described in the above-referenced Andreiko et al. patents. Alternatively, the initial and final tooth positions can be used to derive data sets representing intermediate tooth positions, which are used to fabricate transparent aligning shells for moving teeth to the final position, as described in the above-referenced Chisti et al. patents. The data can also be used to place brackets and design a customized archwire as described in the previously cited application Ser. No. 09/835,039.

To facilitate sharing of the virtual patient model among specialists and device manufacturers, the system 100 includes software routines and appropriate hardware devices for transmitting the virtual patient model or some subset thereof over a computer network. The system's software instructions are preferably integrated with a patient management program having a scheduling feature for scheduling appointments for the patient. The patient management program provides a flexible scheduling of patient appointments based on progress of treatment of the craniofacial anatomical structures. The progress of treatment can be quantified. The progress of treatment can be monitored by periodically obtaining updated three-dimensional information regarding the progress of treatment of the craniofacial features of the patient, such as by obtaining updated scans of the patient and comparison of the resulting 3D model with the original 3D model of the patient prior to initiation of treatment.

Thus, it is contemplated that system described herein provides a set of tools and data acquisition and processing subsystems that together provides a flexible, open platform or portal to a variety of possible therapies and treatment modalities, depending on the preference of the patient and the practitioner. For example, a practitioner viewing the model and using the treatment planning tools may determine that a patient may benefit from a combination of customized orthodontic brackets and wires and removable aligning devices. Data from the virtual patient models is provided to diverse manufacturers for coordinated preparation of customized appliances. Moreover, the virtual patient model and powerful tools described herein provide a means by which the complete picture of the patient can be shared with other specialists (e.g., dentists, maxilla-facial or oral surgeons, cosmetic surgeons, other orthodontists) greatly enhancing the ability of diverse specialists to coordinate and apply a diverse range of treatments to achieve a desired outcome for the patient. In particular, the overlay or superposition of a variety of image information, including 2D X-Ray, 3D teeth image data, photographic data, CT scan data, and other data, and the ability to toggle back and forth between these views and simulate changes in position or shape of craniofacial structures, and the ability to share this virtual patient model across existing computer networks to other specialists and device manufacturers, allows the entire treatment of the patient to be simulated and modeled in a computer. Furthermore, the expected results can be displayed before hand to the patient and changes made depending on the patient input.

With the above general description in mind, additional details of presently preferred components and aspects of the inventive system and the software modules providing the functions referenced above will be described next.

Bracket-Slot-to-Wire Play Compensation

For orthodontic treatment of a patient, orthodontic archwires are used to apply forces to brackets bonded onto the patient's teeth to move the teeth into the desired positions for achieving the target of the treatment. The archwire is inserted into the bracket slots; therefore it is of a smaller cross-section than the bracket slots.

During the treatment planning process, customized archwires are designed based upon the individual treatment goals (target positions of teeth) and individual bracket positions on the teeth to increase the effectiveness of the archwires in achieving the treatment goals. Customized archwires comprise alternating sliding segments interconnected by segments with bends and/or twists in three-dimensional space. Sliding segments may comprise either straight or smoothly curved segments or a combination thereof. The sliding segments are placed in the bracket slots and exert forces on the brackets for moving the teeth towards the target positions. However, the effectiveness of a customized archwire can be reduced when one or more archwire segments fail to engage the bracket slots properly due to the extra space surrounding the archwire segments occupying the bracket slots, since the archwires cross-sections, as discussed above, are smaller in dimensions then the bracket slots they occupy. The space between a bracket slot and a sliding segment of the archwire occupying the bracket slot is hereinafter referred to as bracket-slot-to-wire play. The preferred embodiment of the invention disclosed herein teaches methods for offsetting the undesired effects of the bracket-slot-to-wire play by properly engaging the archwire in the bracket slots. The scope of the customized archwire design is expanded to include positioning the geometry of the archwire sliding segments in relation to the bracket slots in order to properly compensate for the bracket-slot-to-wire play.

Figure 2B:
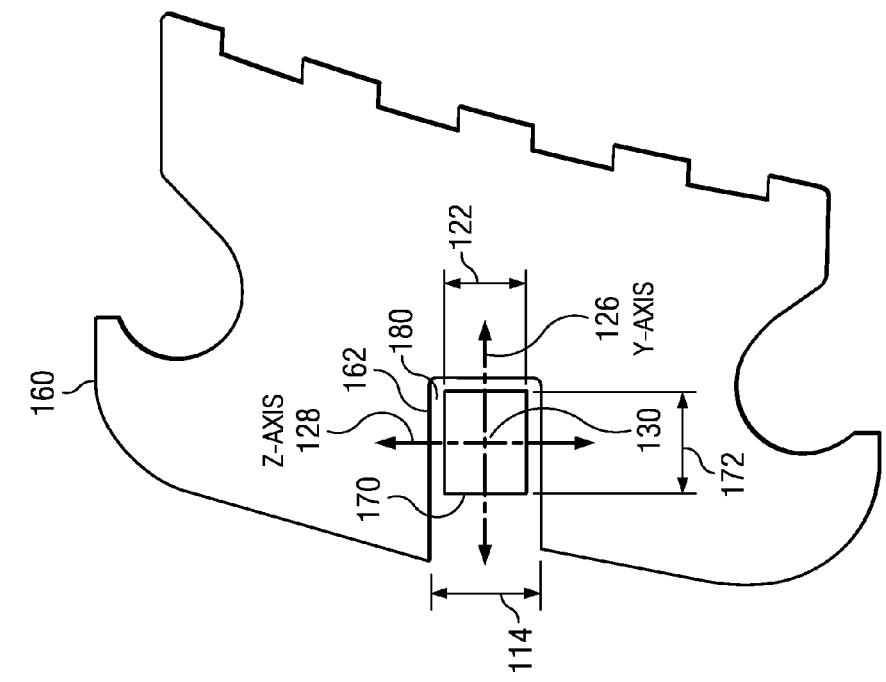
FIG. 2B shows a cross-sectional view of the bracket and the archwire sliding segment shown in FIG. 2A.
Figure 2A:
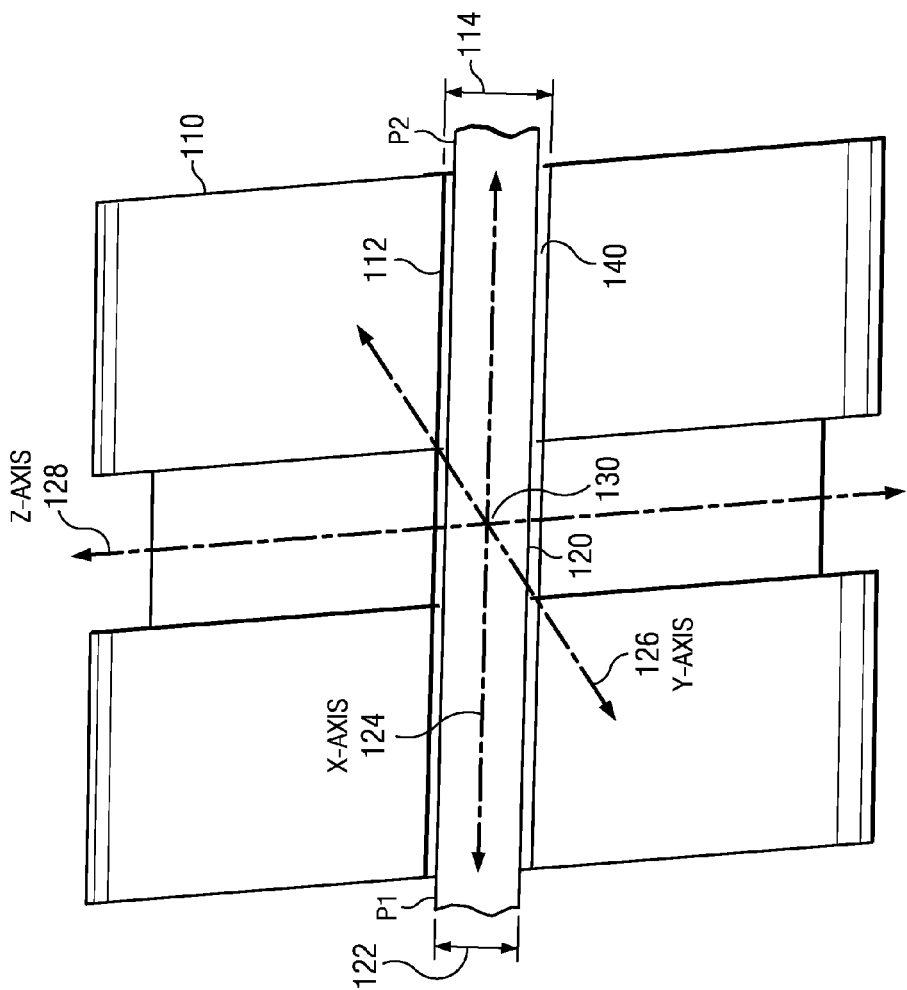
FIG. 2A shows the front-view of an example bracket and an example archwire sliding segment inserted in the slot of the bracket.

FIGS. 2A and 2B illustrate in detail the concept of the bracket-slot-to-wire play.

FIG. 2A shows the front-view of an example bracket 110 with slot 112 having the width 114. An example archwire sliding segment 120 having width 122 is inserted in the slot 112 of bracket 110. The archwire sliding segment 120 has x-axis 124, y-axis 126 and z-axis 128 with x-axis, y-axis and z-axis crossing at the center 130. Axes x, y and z are orthogonal to each other. The bracket-slot-to-wire play 140 in this case is the space between the bracket slot 112 and the archwire sliding segment 120.

FIG. 2B shows a cross-sectional view 160 of the bracket 110 and the cross-sectional view 170 of the archwire sliding segment 120, both shown in FIG. 2A, taken at the z-axis plane in FIG. 2A and viewed from the direction A. The sliding segment is generally straight, however, one skilled in the art would appreciate the sliding segment having a smoothly curved shape. The bracket slot cross-section 162 has the width 114 the same as in FIG. 2A. The archwire cross-section 170 has the width 122 the same as in FIG. 2A, and the height 172. For the archwire cross-section 170, the y-axis 126 and the z-axis 128 and the center 130 remain the same as in FIG. 2A. The bracket-slot-to-wire play 180 is the space surrounding the archwire cross-section 170 bounded by the bracket slot cross-section 162. Although the archwire cross-section 170 shown in FIG. 2B is rectangular in shape with sharp or unrounded edges, one skilled in the art would appreciate that the archwires with cross-sections having variety of geometrical shapes, such as for example, square with sharp edges, rectangular with rounded edges, square with rounded edges, elliptical, round, etc. are possible.

Figure 3:
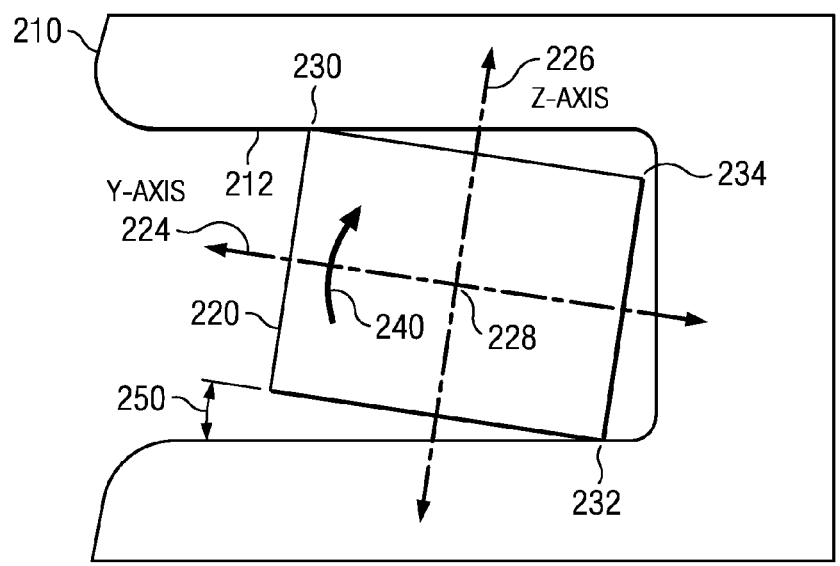
FIG. 3 is similar to FIG. 2B and shows the cross-section of the bracket and the archwire shown in FIG. 2A with the archwire rotated to apply torque.

As a typical deficiency, the bracket-slot-to-wire play prevents an archwire from exerting the desired torque to move a tooth in the facial or lingual direction. According to the preferred embodiment of the invention, this deficiency can be offset by properly rotating (or twisting) the sliding segment of the archwire along the long axis of the wire or x-axis. FIG. 3 shows an enlarged view of the cross-section of the bracket 210 which is similar to the bracket cross section 160 in FIG. 2B. In order to achieve the desired torque the sliding segment of the archwire going through the bracket slot 212 is rotated such that its cross-section 220 engages the walls of the bracket slot at points 230 and 232, and optionally at point 234 as well. In order to explain the nature of rotation a reference to FIGS. 2A and 2B will now be made. Imagine that in FIG. 2A, the archwire sliding segment 120 is rotated or twisted uniformly between the end points P1 and P2 of the archwire sliding segment 120 along the x-axis 124 until the diagonally opposite corner-points of the archwire cross-section 170 of FIG. 2B touch the walls of the bracket slot 162 in FIG. 2B. The same type of rotation as described above is made of the archwire having the cross-section 220 and around the center point 228 in FIG. 3. The direction of rotation 240 of the archwire causes the archwire cross-section 220 rotated by degrees identified by the angle 250. The y-axis 224 and the z-axis 226 moved as a result of the rotation in the positions shown in FIG. 3. One skilled in the art would appreciate that if the desired torque is facial torque than the rotation of the archwire would be in the facial direction; whereas if the desired torque is lingual, then the rotation of the archwire would be in the lingual direction, opposite to the direction for the facial torque.

Figure 4A:
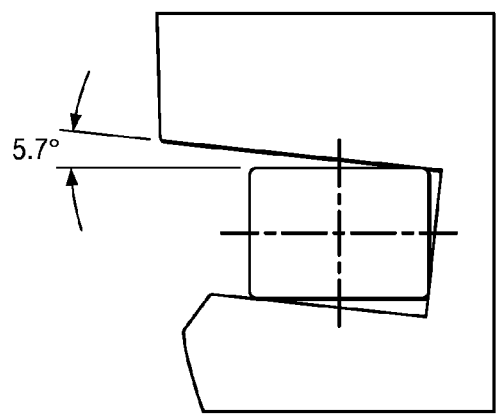
FIG. 4A shows an example bracket-slot with industry standard specification of width; and an example archwire with industry standard specification. The archwire has rectangular cross-section with sharp un-rounded edges.
Figure 4B:
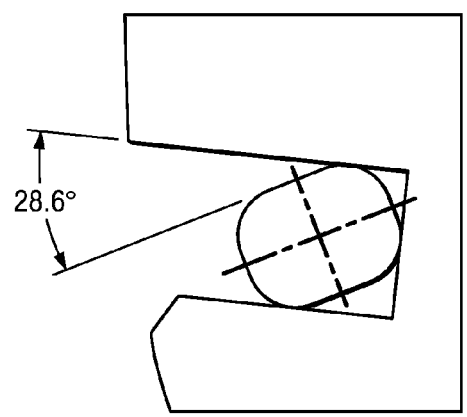
FIG. 4B shows an example bracket-slot and an example archwire with industry standard specifications the same as in FIG. 4A; however, the archwire in FIG. 4B has rectangular cross-section with rounded edges.

The amount of the bracket-slot-to-wire play is determined by the size of the bracket slot and the size of the archwire in terms of its cross section. The bracket slots are specified in terms of the width dimension with a tolerance; and the archwires are specified in terms of the cross-section and tolerances. One can use the data supplied by the manufacturers of the brackets and the archwires to compute the size of the bracket-slot-to-wire play. Alternately, one can scan the bracket and the archwire of interest to determine the actual size of the bracket slot and the archwire cross-section inorder to determine the actual value of the bracket-slot-to-wire play. FIG. 4A shows an example bracket-slot with industry standard specification of width equal to 0.46 mm+0.04 mm tolerance; and an example archwire with cross-section of 0.41 mm−0.01 mm tolerance×0.56 mm−0.01 mm tolerance; and rounded edges with a small radius. The archwire has rectangular cross-section with sharp un-rounded edges (or edges rounded with a very small radius not shown in this figure). The degree of rotation of the sliding segment of the archwire that can be realized in this case is 5.7°. FIG. 4B shows the same bracket slot and the archwire combination as in FIG. 4A, with the exception that the archwire cross-section has rounded edges with a larger radius. The resulting degree of rotation of the sliding segment of the archwire that can be realized is 28.6°. One skilled in the art would appreciate the calculation of the bracket-slot-to-wire play required for a smoothly curved segment can be done at the first contact point of the wire and the bracket slot. In the symmetric case, this can be done at the midpoint of the sliding segment.

Figure 5:
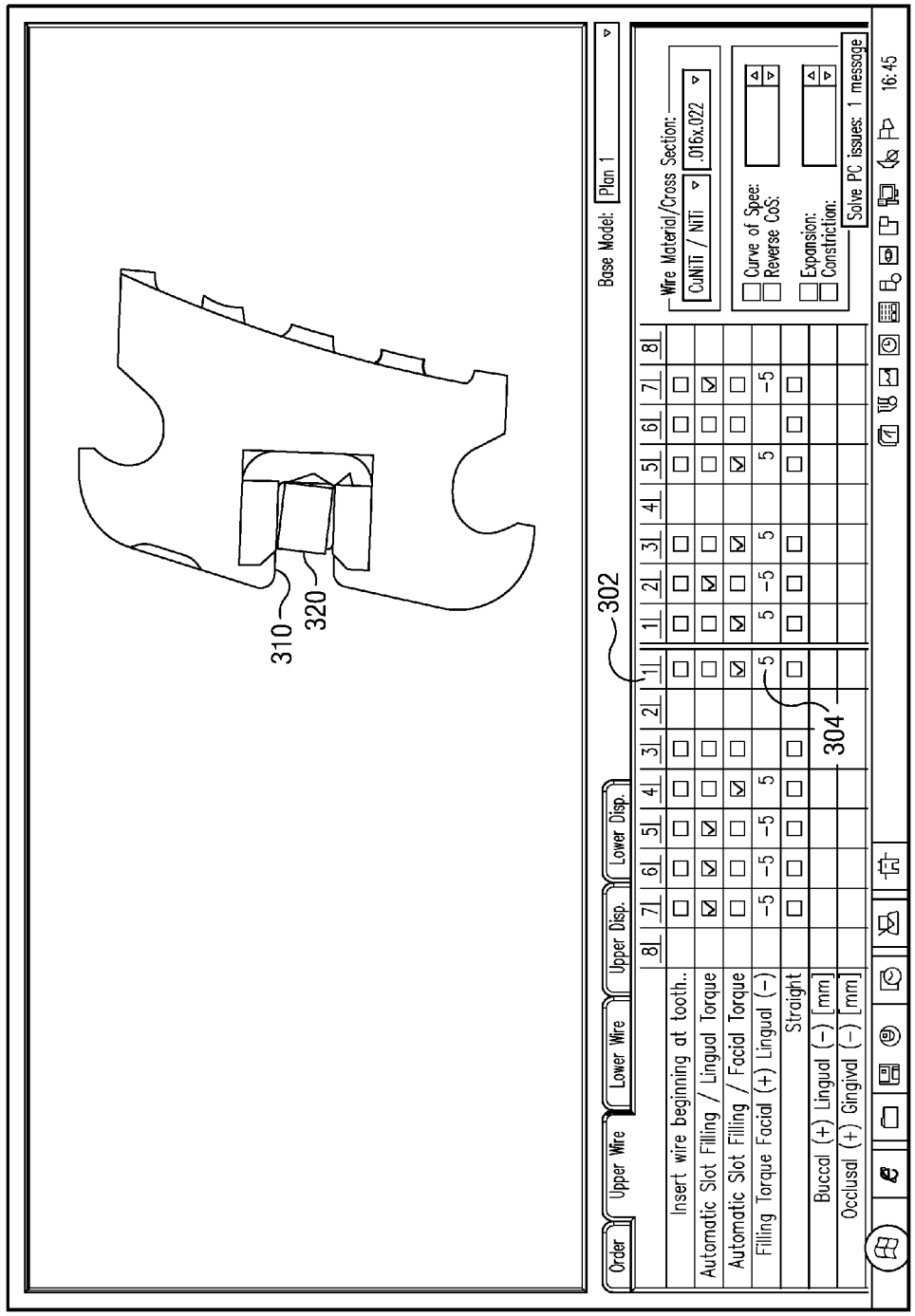
FIG. 5 shows an example where a tooth requires facial torque, which has been automatically calculated by the treatment planning software.

FIG. 5 shows an example where the tooth 302 requires facial torque and an additional slot-filling torque 304 in the amount of 5°, which has been automatically calculated by the treatment planning software to fully engage the bracket slot. FIG. 5 also shows the slot 310 for the bracket associated with tooth 302 and the archwire cross-section 320 rotated in the facial direction to fully engage the bracket.

Figure 6:
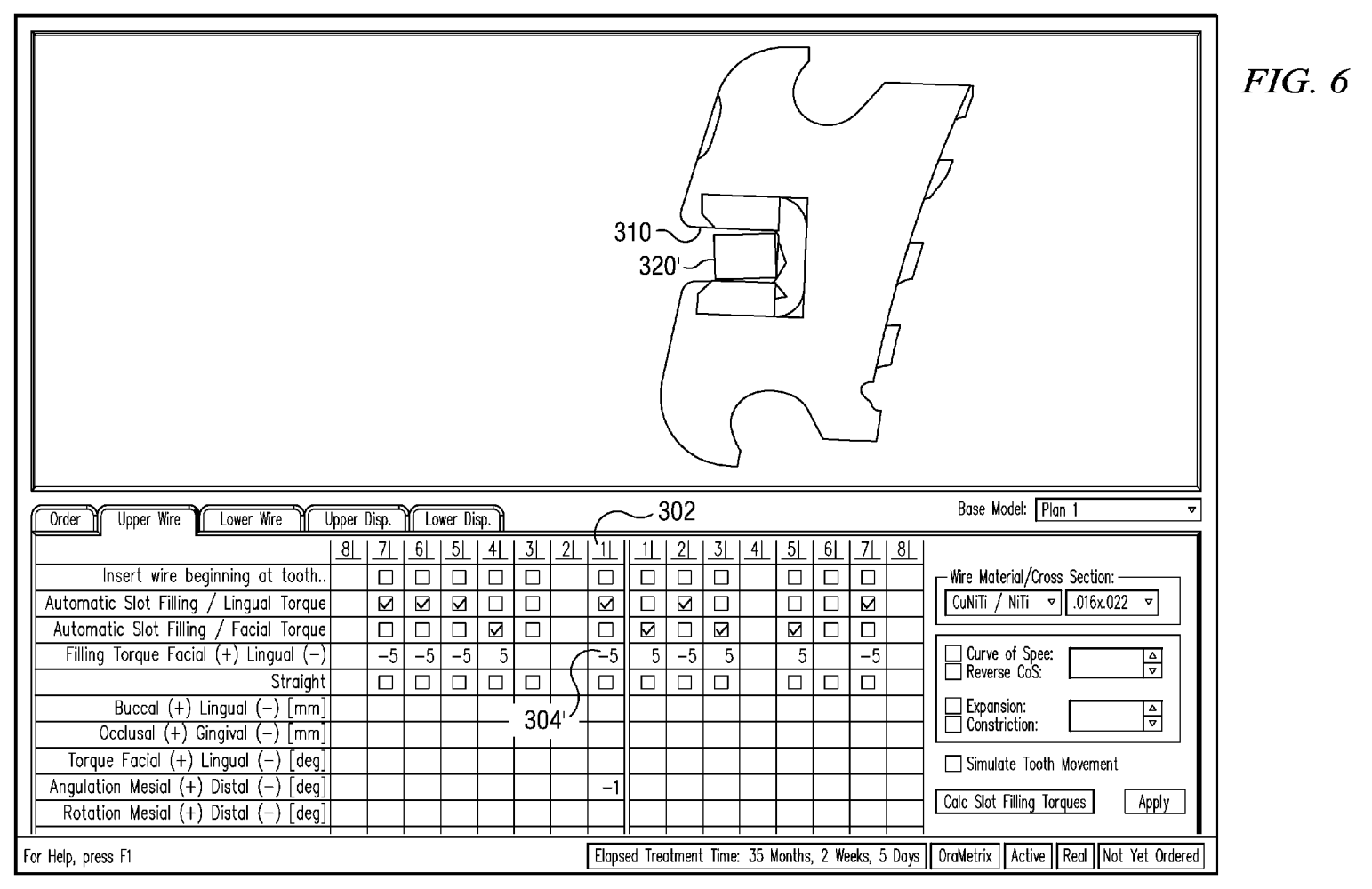

FIG. 6 shows the same example tooth 302 as in FIG. 5. However, if the practitioner desires lingual tooth movement, the automatic determination by the treatment planning software changes the additional slot-filling torque 304' to a lingual torque in the amount of −5°. FIG. 6 shows the same slot 310 for the bracket as in FIG. 5 associated with tooth 302. However, the archwire cross-section 320' is now rotated in the lingual direction to fully engage the bracket.

Figure 7:
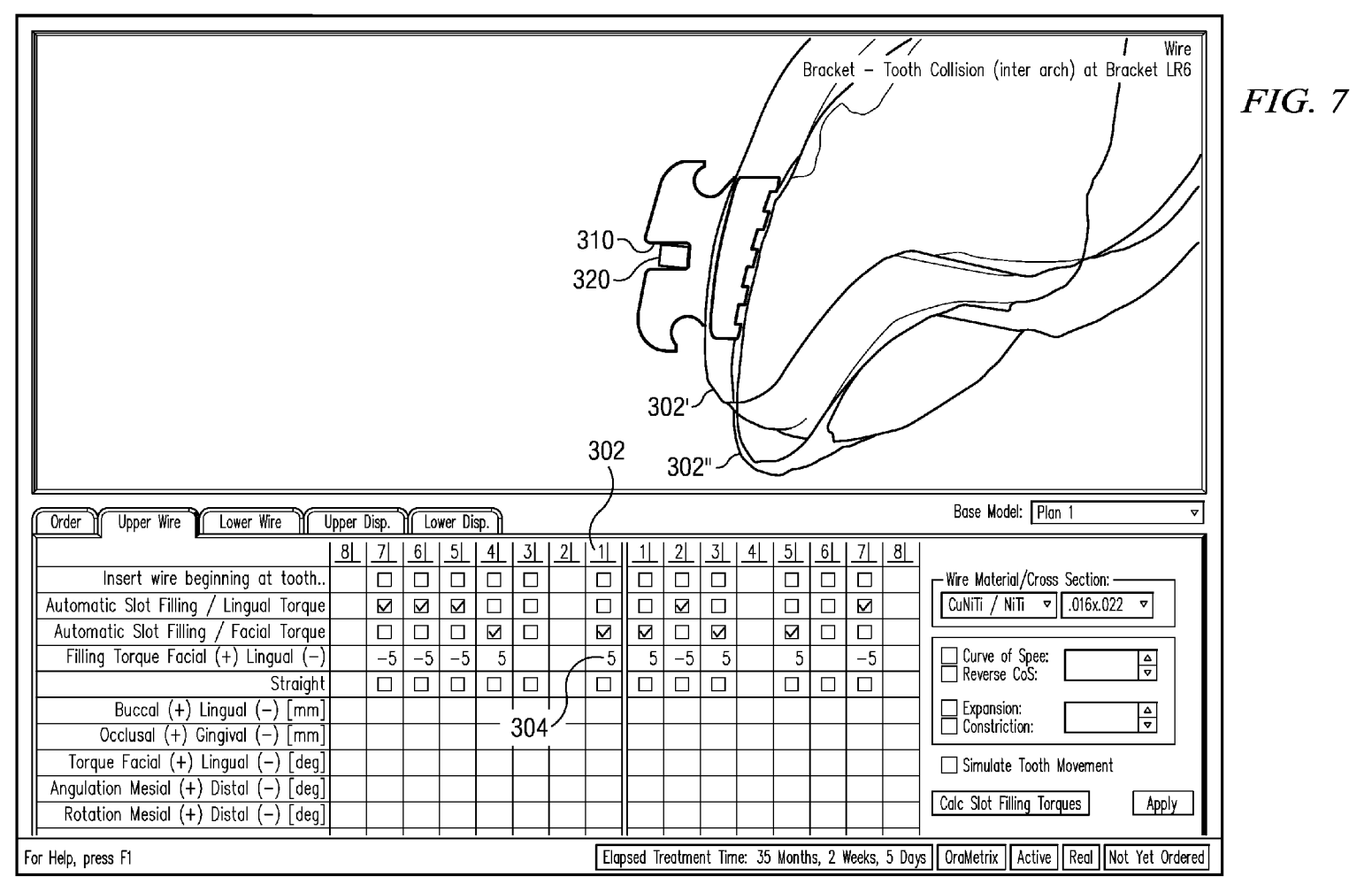

FIG. 7 shows the same example tooth 302 as in FIG. 5. Tooth 302 is shown in two different positions, namely the tooth 302 in the target position 302" superimposed over the tooth 302 in the initial position 302'. The bracket with the slot 310 is shown bonded to the target position 302". The archwire cross-section 320 is shown in the rotated position just the same as in FIG. 5 for delivering the facial torque with the additional slot-filling torque 304 in the amount of 5°. The tooth 302 in the target position 302" superimposed over the tooth 302 in the initial position 302' is shown in the form of a cross-section made possible by the clipping plane tool in the treatment planning software.

Figure 8A:
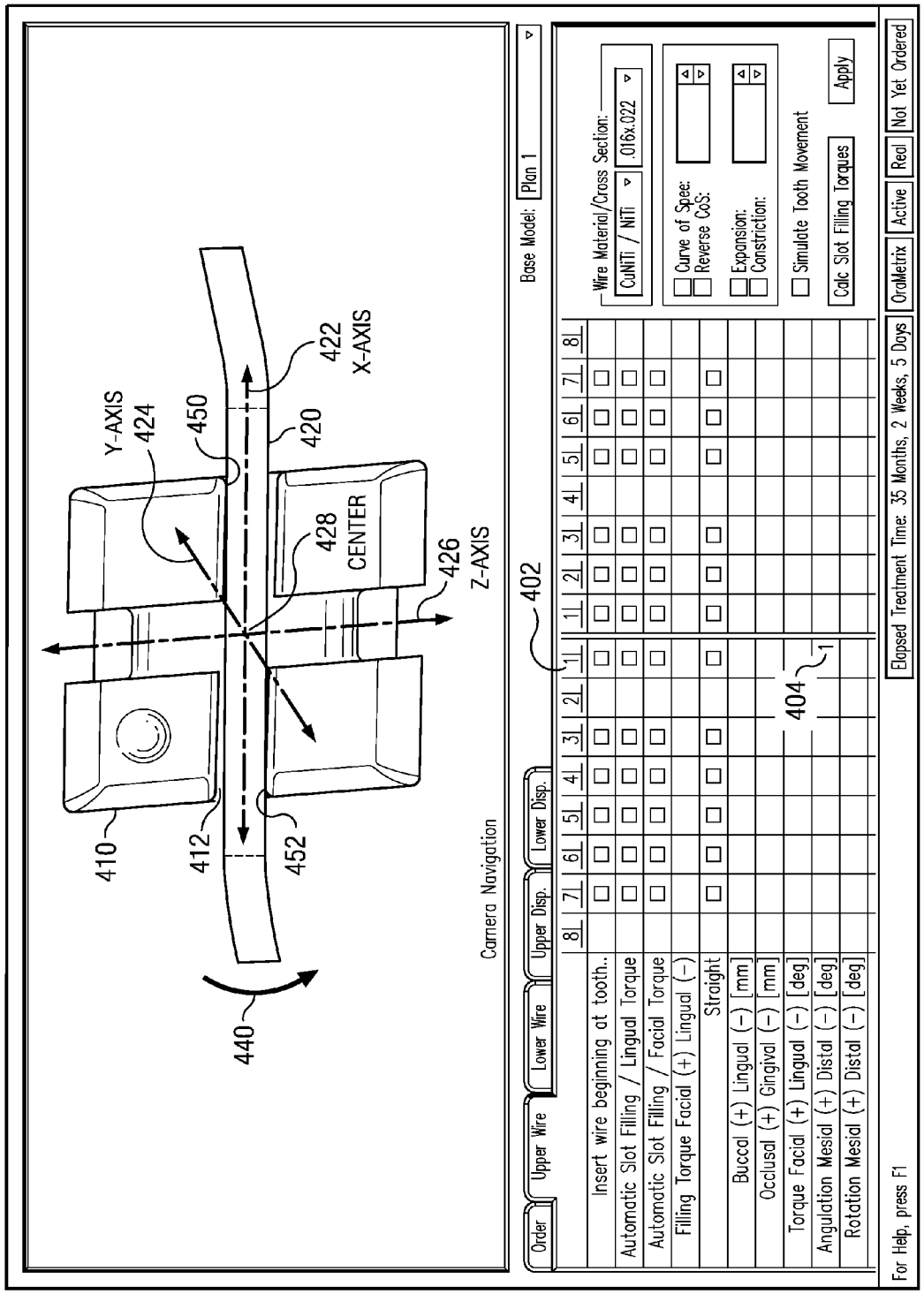
FIG. 8A shows that a tooth requires a mesial angulation. The straight archwire segment is rotated around the y-axis in the mesial direction such that the straight archwire segment makes surface contact with the walls of the bracket slot at two locations. This type and amount of offset would provide the desired degree of mesial angulation.

As another deficiency, the bracket-slot-to-wire play prevents an archwire from exerting the desired angulation force to move a tooth in the mesial or distal direction. According to another preferred embodiment of the invention, this deficiency can be offset by properly rotating the sliding segment of the archwire around the y-axis of the wire. FIG. 8A shows that a tooth 402 labeled as 1 requires an additional slot-filling mesial angulation 404 of 1°. Bracket 410 is associated with tooth 402. The bracket slot 412 is engaged by straight archwire segment 420. The straight archwire segment 420 has x-axis 422, y-axis 424, z-axis 426 and the center 428. In order to provide the desired mesial angulation, the straight archwire segment 420 is rotated around the center 428 in the rotation direction 440 such that the straight archwire segment 420 makes surface contact with the walls of the bracket slot 412 at locations 450 and 452.

Figure 8B:
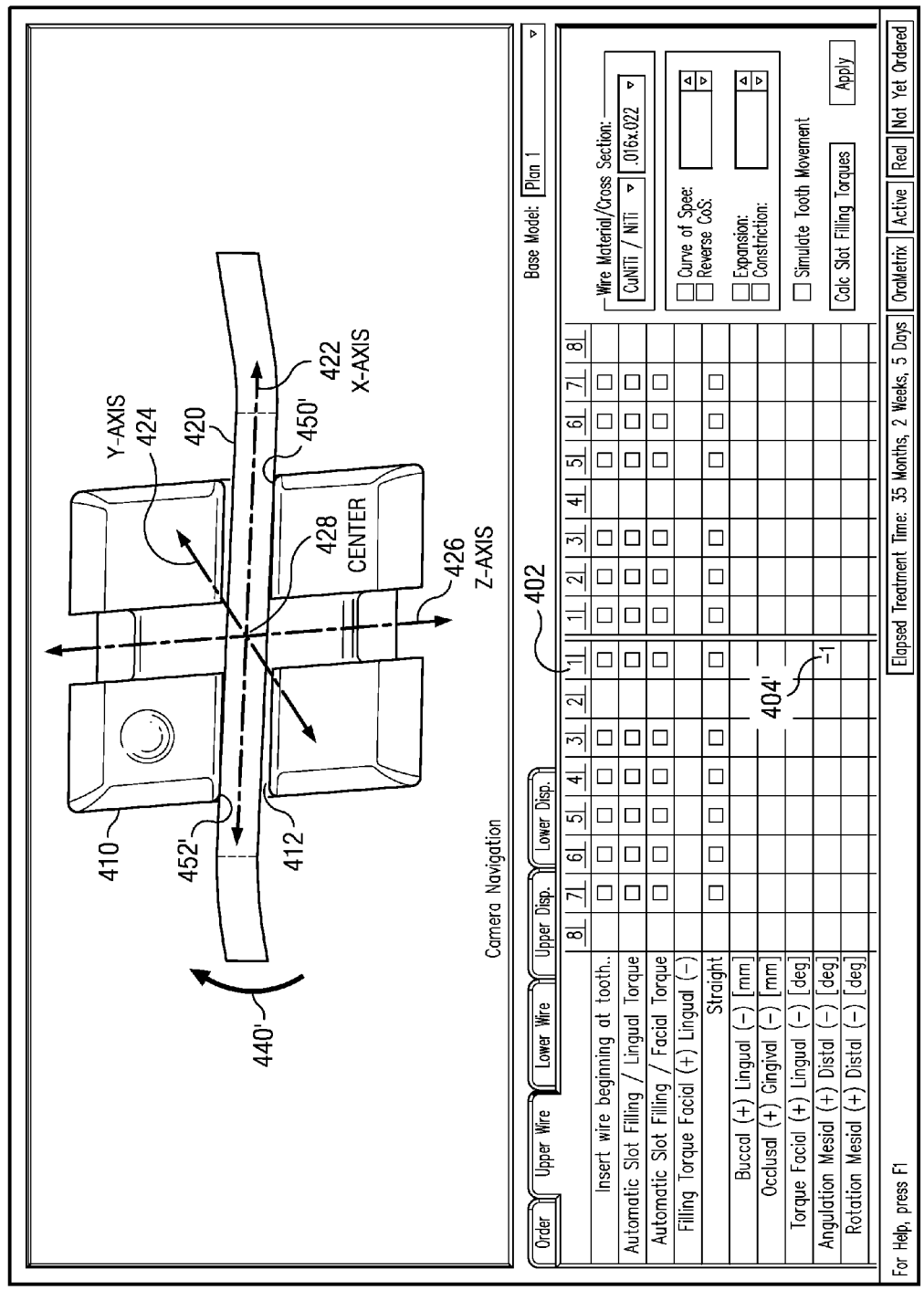
FIG. 8B is similar to FIG. 8A with the exception that FIG. 8B shows that a tooth requires a distal angulation. In this case, the straight archwire segment is rotated around the y-axis in the distal direction such that the straight archwire segment makes surface contact with the walls of the bracket slot at two locations. This type and amount of offset would provide the desired degree of distal angulation.

FIG. 8B is very similar to FIG. 8A, except that the tooth 402 labeled as 1 in this case requires an additional slot-filling distal angulation 404' of −1°. Bracket 410 remains associated with tooth 402. The bracket slot 412 is engaged by straight archwire segment 420. The straight archwire segment 420 has x-axis 422, y-axis 424, z-axis 426 and the center 428. In order to provide the desired mesial angulation, the straight archwire segment 420 is rotated around the center 428 in the rotation direction 440' such that the straight archwire segment 420 makes surface contact with the walls of the bracket slot 412 at locations 450' and 452'.

As yet another deficiency, the bracket-slot-to-wire play prevents an archwire from exerting the desired force to rotate a tooth in the mesial or distal direction. According to yet another preferred embodiment of the invention, this deficiency can be offset by properly rotating the sliding segment of the archwire around z-axis. In order to explain this embodiment of the invention, reference is made back to FIG. 2A. The archwire sliding segment 120 is rotated around the z-axis 128 either in the mesial direction if the mesial rotation is desired, or in the distal direction if the distal rotation is desired, until the archwire comes in firm contact with the bottom wall of the bracket-slot occupied by the archwire.

As yet another deficiency, the bracket-slot-to-wire play prevents an archwire from exerting the desired translational force to move a tooth in the buccal or lingual direction. According to yet another preferred embodiment of the invention, this deficiency can be offset by properly moving the sliding segment of the archwire along y-axis. In order to explain this embodiment of the invention, reference is made again back to FIG. 2A. The archwire sliding segment 120 is moved along y-axis 126 either in the buccal direction if the buccal translation is desired, or in the lingual direction if the lingual translation is desired. O-rings or wire-ties are placed on the bracket in order to keep the archwire within the bracket slot and can be used to achieve the buccal movement. On the other hand when the translational movement of the archwire segment in the lingual direction is required then the archwire is moved in the lingual direction until it comes in firm contact with the bottom of the bracket-slot occupied by the archwire.

As yet another deficiency, the bracket-slot-to-wire play prevents an archwire from exerting the desired translational force to move a tooth in the occlusal or gingival direction. According to yet another preferred embodiment of the invention, this deficiency can be offset by properly moving the sliding segment of the archwire along z-axis. In order to explain this embodiment of the invention, reference is made again back to FIG. 2A. The archwire sliding segment 120 is moved along z-axis 128 either in the occlusal direction if the occlusal translation is desired, or in the gingival direction if the gingival translation is desired. When the translational movement of the archwire segment in the occlusal direction is required then the archwire is moved in the occlusal direction until it comes in firm contact with the lower side wall of the bracket-slot occupied by the archwire. On the other hand when the translational movement of the archwire segment in the gingival direction is required then the archwire is moved in the gingival direction until it comes in firm contact with the upper side wall of the bracket-slot occupied by the archwire.

In summary, the deficiencies caused by the bracket-slot-to-wire play by disabling an archwire from exerting the desired force in any of the 5-degrees of freedom, namely torque (facial and lingual), angulation (mesial and distal), rotation (mesial and distal), buccal and lingual translation and occlusal and gingival translation, can be offset by the various embodiments of the invention disclosed above. A user can manually or automatically identify the type of deficiency caused by the bracket-slot-to-wire play, given bracket slot size and the archwire cross section parameters, and manually or automatically determine the method of offsetting the deficiency, by using the software tools available in the treatment planning workstation. The desired offset for the compensation of the bracket-slot-to-wire play is displayed on the display of the treatment planning workstation. The user can override the offset automatically determined by the treatment planning software and simulate and design the archwire based upon the offset determined to be more desirable by the user or the practitioner. If the desired tooth position cannot be achieved with a single offset, then the practitioner may choose to accomplish that in multiple stages of the tooth movement during the course of the treatment by changing the design of the archwire as the treatment progresses. Also, it is possible that multiple types of deficiencies may be caused by the bracket-slot-to-wire play. In that case the practitioner may choose to combine the remedies for one or more deficiencies using the procedure described above for each degree of freedom, i.e. torque, angulation, rotation and buccal-lingual and occlusal-gingival translations; or approach the remedies in treatment stages.

Figure 9:
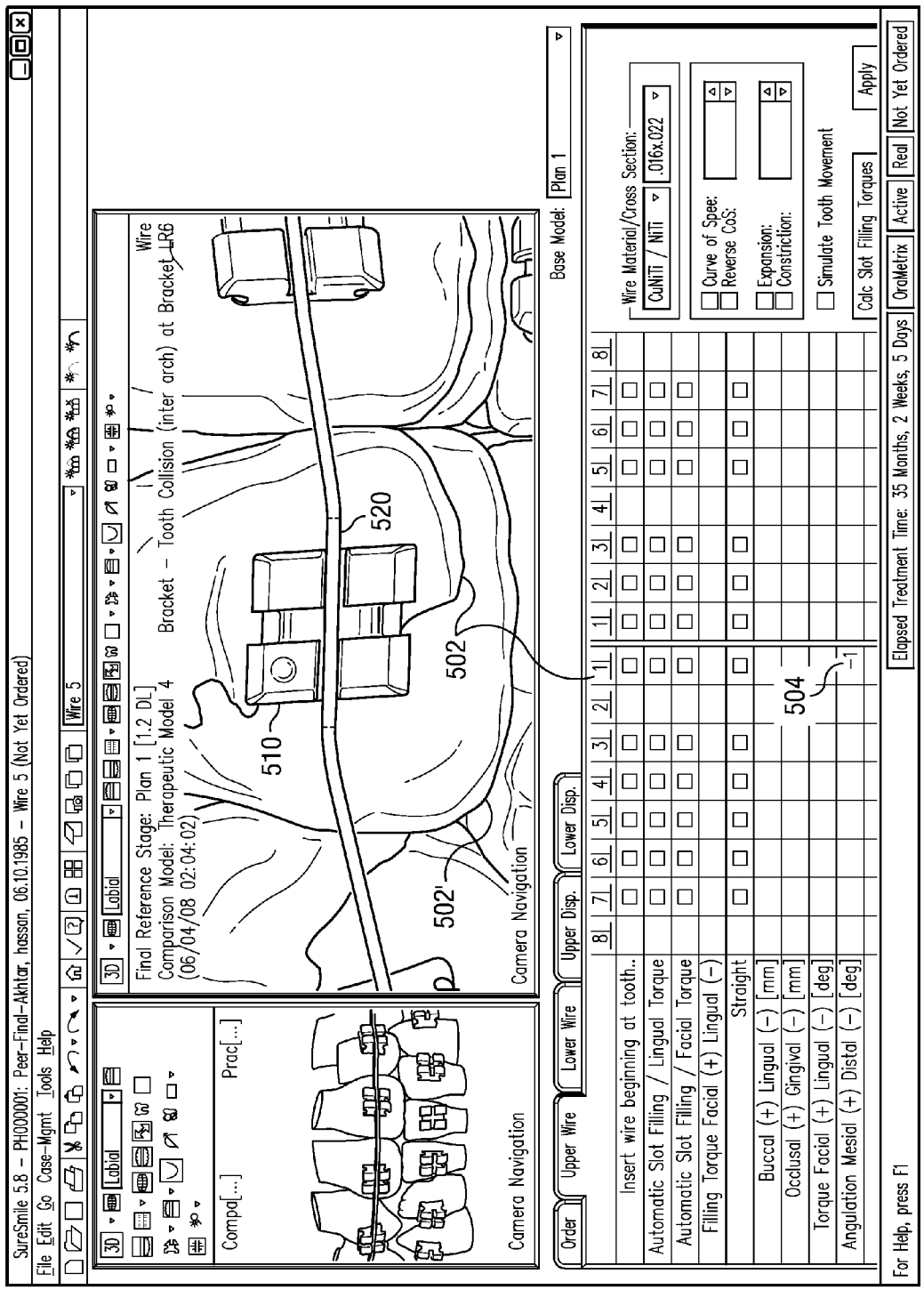
FIG. 9 illustrates the process of designing the desired offset to compensate for the bracket-slot-to-wire play by way of an example.

FIG. 9 illustrates the process of designing the desired offset to compensate for the bracket-slot-to-wire play by way of an example. In this figure, the user has selected tooth 502 in the upper jaw of the patient. Digital or virtual models of the patient's teeth in the initial positions as well as the target or set-up positions are available. FIG. 9 shows a portion of the selected tooth in the initial position 502 along with a portion of the same tooth in the target or set-up position 502'. In this example the desired tooth displacement from the initial position to the target position requires one additional degree of distal angulation 504 (shown as −1 in FIG. 9) to fully engage the bracket slot. The desired displacement can be realized by adjusting the sliding segment 520 of the archwire, which is inserted into the slot of the bracket 510 shown bonded to the tooth in the target position 502', using the procedure described earlier for designing the archwire for handling angulation displacement. The new customized design of the archwire segment to compensate for the bracket-slot-to-wire play will be included in the prescription to bend the archwire. One skilled in the art would appreciate that this methodology of designing the compensation for bracket-slot-to-wire play can be applied to plurality of teeth for designing the customized archwire. The process can be carried out by the practitioner in the practitioner's office, at the 'chair-side while examining the patient' if so desired, or at a different location away from the practitioner's office using the internet as a vehicle of communication between different workstations.

In summary then, according to the preferred embodiment of the invention, the procedure described below is utilized to realize compensation for the bracket-slot-to-wire play.

1. Quantify the bracket-slot-to-wire play.
   (a) This can be accomplished if one of the following items is known.
      i. ideal slot size and ideal archwire cross-section;
      ii. tolerance model of slot and tolerance model of the archwire cross-section;
      iii. actual (measured) model of slot and actual (measured) model of the archwire cross-section (for each individual item or on a lot bases); or
      iv. every possible combination of the above three items.
   (b) It can be determined from the actual and target positions of bracket slots.
2. Then the offset to compensate for the bracket-slot-to-wire play can be determined as follows:
   a. Calculate the slot play between the bracket-slot and the height of the archwire.
   b. Calculate the direction of the intended movement in coordinates of the bracket slot. (i.e., initial or actual to target or set-up)
   c. Calculate the maximum possible rotation or translation of the archwire sliding segment in the bracket-slot, so that the sides or the edges of the archwire touch the sides of the walls of the bracket-slot, based upon the direction of the information from step 2.b.

The bracket-slot-to-wire play offsetting compensations are made part of the customized archwire design and included in the prescription for manufacturing the customized archwire.

While presently preferred embodiments of the invention have been described for purposes of illustration of the best mode contemplated by the inventors for practicing the invention, wide variation from the details described herein is foreseen without departure from the spirit and scope of the invention. This true spirit and scope is to be determined by reference to the appended claims. The term "bend", as used in the claims, is interpreted to mean either a simple translation movement of the work-piece in one direction or a twist (rotation) of the work-piece, unless the context clearly indicates otherwise.

The invention claimed is:

1. A method for offsetting one or more undesired effects of bracket-slot-to-wire play comprising space between a bracket slot and a sliding segment of a customized archwire occupying said bracket slot, wherein said customized archwire comprises alternating sliding straight segments interconnected by segments with bends and/or twists in three-dimensional space, using a workstation, comprising the steps of:
   a obtaining data from orthodontic treatment plan of a patient comprising planned displacements of teeth, type and placement of brackets on said teeth of said patient, and customized archwire;
   b selecting a tooth of said patient, and identifying bracket assigned to said tooth and segment of said customized archwire designated for sliding through slot in said bracket;
   c obtaining dimensions of said slot in said bracket;
   d obtaining dimensions of cross-section of said archwire;
   e calculating bracket-slot-to-wire play for said sliding archwire segment from said dimensions of said slot in said bracket and said dimensions of said cross-section of said archwire; and
   f determining compensation into said sliding archwire segment for offsetting said one or more undesired effects from said bracket-slot-to-wire play in order to realize said planned displacement of said tooth of said patient during said orthodontic treatment.

2. The method of claim 1, wherein said dimensions of said slot in said bracket are determined from data supplied by manufacturer of said bracket.

3. The method of claim 1, wherein said dimensions of said slot in said bracket are determined from scanning data of said bracket.

4. The method of claim 1, wherein said dimensions of said cross-section of said section of said archwire are determined from data supplied by manufacturer of said archwire.

5. The method of claim 1, wherein said dimensions of said cross-section of said section of said archwire are determined from scanning data of said archwire.

6. The method of claim 1, wherein said planned displacement of said tooth requires torque to move said tooth in facial direction.

7. The method of claim 1, wherein said planned displacement of said tooth requires torque to move said tooth in labial direction.

8. The method of claim 1, wherein said planned displacement of said tooth requires angulation force to move said tooth in mesial direction.

9. The method of claim 1, wherein said planned displacement of said tooth requires angulation force to move said tooth in distal direction.

10. The method of claim 1, wherein said planned displacement of said tooth requires rotation to move said tooth in mesial direction.

11. The method of claim 1, wherein said planned displacement of said tooth requires rotation to move said tooth in distal direction.

12. The method of claim 1, wherein said planned displacement of said tooth requires translational force to move said tooth in buccal direction.

13. The method of claim 1, wherein said planned displacement of said tooth requires translational force to move said tooth in lingual direction.

14. The method of claim 1, wherein said planned displacement of said tooth requires translational force to move said tooth in occlusal direction.

15. The method of claim 1, wherein said planned displacement of said tooth requires translational force to move said tooth in gingival direction.

16. The method of claim 1, wherein said planned displacement of said tooth requires combination of forces to move said tooth in two or more directions using facial or lingual torque, mesial or distal angulation, mesial or distal rotation, buccal or lingual translation and occlusal or gingival translation.

17. The method of claim 1, wherein said compensation of said section of said archwire is realized through rotation of said section of said archwire.

18. The method of claim 1, wherein said compensation of said section of said archwire is realized through twist of said section of said archwire.

19. The method of claim 1, wherein said desired displacement of said tooth requires combination of forces to move said tooth in two or more directions using facial or lingual torque, mesial or distal angulation, mesial or distal rotation, buccal or lingual translation and occlusal or gingival translation; wherein said combination of forces are realized through stages of compensation of said section of said archwire.

20. The method of claim 1, wherein said compensation is automatically determined using said workstation.

21. The method of claim 1, wherein planned offset of said compensation is displayed on display of said workstation.

22. A workstation for expanding the process for designing a customized archwire for offsetting one or more undesired effects of bracket-slot-to-wire play comprising space between a bracket slot and a sliding segment of a customized archwire occupying said bracket slot, wherein said customized archwire comprises alternating sliding straight segments interconnected by segments with bends and/or twists in three-dimensional space, comprising:
  a computing device;
  a data storage device;
  a display; and
  software instructions for:
    a obtaining data from orthodontic treatment plan of a patient comprising planned displacements of teeth, type and placement of brackets on said teeth of said patient, and customized archwire;
    b selecting a tooth of said patient, and identifying bracket assigned to said tooth and segment of said customized archwire designated for sliding through slot in said bracket;
    c obtaining dimensions of said slot in said bracket;
    d obtaining dimensions of cross-section of said archwire;
    e calculating bracket-slot-to-wire play for said sliding archwire segment from said dimensions of said slot in said bracket and said dimensions of said cross-section of said archwire; and
    f determining compensation into said sliding archwire segment for offsetting said bracket-slot-to-wire play in order to realize said planned displacement of said tooth of said patient during said orthodontic treatment.

23. The workstation of claim 22, wherein said dimensions of said slot in said bracket are determined from data supplied by manufacturer of said bracket.

24. The workstation of claim 22, wherein said dimensions of said slot in said bracket are determined from scanning data of said bracket.

25. The workstation of claim 22, wherein said dimensions of said cross-section of said section of said archwire are determined from data supplied by manufacturer of said archwire.

26. The workstation of claim 22, wherein said dimensions of said cross-section of said section of said archwire are determined from scanning data of said archwire.

27. The workstation of claim 22, wherein said planned displacement of said tooth requires torque to move said tooth in facial direction.

28. The workstation of claim 22, wherein said planned displacement of said tooth requires torque to move said tooth in labial direction.

29. The workstation of claim 22, wherein said planned displacement of said tooth requires angulation force to move said tooth in mesial direction.

30. The workstation of claim 22, wherein said planned displacement of said tooth requires angulation force to move said tooth in distal direction.

31. The workstation of claim 22, wherein said planned displacement of said tooth requires rotation to move said tooth in mesial direction.

32. The workstation of claim 22, wherein said planned displacement of said tooth requires rotation to move said tooth in distal direction.

33. The workstation of claim 22, wherein said planned displacement of said tooth requires translational force to move said tooth in buccal direction.

34. The workstation of claim 22, wherein said planned displacement of said tooth requires translational force to move said tooth in lingual direction.

35. The workstation of claim 22, wherein said planned displacement of said tooth requires translational force to move said tooth in occlusal direction.

36. The workstation of claim 22, wherein said planned displacement of said tooth requires translational force to move said tooth in gingival direction.

37. The workstation of claim 22, wherein said planned displacement of said tooth requires combination of forces to move said tooth in two or more directions using facial or lingual torque, mesial or distal angulation, mesial or distal rotation, buccal or lingual translation and occlusal or gingival translation.

38. The workstation of claim 22, wherein said compensation of said section of said archwire is realized through rotation of said section of said archwire.

39. The workstation of claim 22, wherein said compensation of said section of said archwire is realized through twist of said section of said archwire.

40. The workstation of claim 22, wherein said desired displacement of said tooth requires combination of forces to move said tooth in two or more directions using facial or lingual torque, mesial or distal angulation, mesial or distal rotation, buccal or lingual translation and occlusal or gingival translation; wherein said combination of forces are realized through stages of compensation of said section of said archwire.

41. The workstation of claim 22, wherein planned offset of said compensation is displayed on said display of said workstation.

* * * * *